(12) United States Patent
Coxam et al.

(10) Patent No.: US 8,138,224 B2
(45) Date of Patent: Mar. 20, 2012

(54) NUTRITIONAL OR THERAPEUTIC COMPOSITION CONTAINING THE COMPOUND OLEUROPEINE OR ONE OF THE DERIVATIVES THEREOF

(75) Inventors: Veronique Coxam, Ceyrat (FR); Leandros Skaltsounis, Melissia (GR); Caroline Puel, Romagnat (FR); Andre Mazur, Cournon d'Auvergne (FR)

(73) Assignee: Institut National de la Recherche Agronomique (INRA), Paris (FR)

( * ) Notice: Subject to any disclaimer, the term of this patent is extended or adjusted under 35 U.S.C. 154(b) by 978 days.

(21) Appl. No.: 10/552,723

(22) PCT Filed: Apr. 9, 2004

(86) PCT No.: PCT/FR2004/050156
§ 371 (c)(1),
(2), (4) Date: Oct. 11, 2005

(87) PCT Pub. No.: WO2004/091591
PCT Pub. Date: Oct. 28, 2004

(65) Prior Publication Data
US 2006/0193931 A1    Aug. 31, 2006

(30) Foreign Application Priority Data
Apr. 11, 2003 (FR) .................................. 03 04584

(51) Int. Cl.
*A61K 31/35* (2006.01)
*A01N 43/16* (2006.01)
(52) U.S. Cl. ........................................... 514/460
(58) Field of Classification Search .................. None
See application file for complete search history.

(56) References Cited

U.S. PATENT DOCUMENTS

| | | | |
|---|---|---|---|
| 5,714,150 A * | 2/1998 | Nachman | 424/769 |
| 6,117,844 A | 9/2000 | Frederickson | |
| 6,440,465 B1 | 8/2002 | Meisner | |
| 6,455,070 B1 | 9/2002 | Voorhees et al. | |
| 6,455,580 B1 | 9/2002 | Frederickson | |
| 7,445,807 B2 * | 11/2008 | Lockwood | 426/656 |
| 2001/0046977 A1 | 11/2001 | Yates | |
| 2002/0010341 A1 | 1/2002 | Mesfin et al. | |
| 2003/0004117 A1* | 1/2003 | Hamdi et al. | 514/25 |
| 2003/0017217 A1 | 1/2003 | Quintanilla Almagro et al. | |

FOREIGN PATENT DOCUMENTS

| | | |
|---|---|---|
| EP | 210 728 | 2/1987 |
| JP | 20022128678 | 5/2002 |
| WO | WO 96/14064 | 5/1996 |
| WO | WO 01/76579 | 10/2001 |
| WO | WO 03/068171 | 8/2003 |

OTHER PUBLICATIONS

Katori et al, "Cyclooxygenase-2: its rich diversity of roles and possible application of its selective inhibitors", Inflamm. res. 49, pp. 367-392 (2000).*

Owen R W et al; "The antioxidant/anticancer potential of phenolic compounds isolated from olive oil"; European Journal of Cancer; 2000; pp. 1235-1247; vol. 36 No. 10; Pergamon Press; Oxford, GB.

* cited by examiner

*Primary Examiner* — Sharmila G. Landau
*Assistant Examiner* — Barbara Frazier
(74) *Attorney, Agent, or Firm* — Jacobson Holman, PLLC

(57) ABSTRACT

The present invention provides a nutritional composition and a pharmaceutical composition to be used for humans or animals comprising as active compound the oleuropein compound or one derivative thereof.

15 Claims, 3 Drawing Sheets

NUTRITIONAL OR THERAPEUTIC COMPOSITION CONTAINING THE COMPOUND OLEUROPEINE OR ONE OF THE DERIVATIVES THEREOF

This is a nationalization of PCT/FR04/050156 filed Apr. 9, 2004 and published in French.

FIELD OF THE INVENTION

The present invention relates to the field aiming at maintaining or restoring the human or animal bone metabolism, especially for preventing or treating disorders associated with a bone metabolism imbalance thanks to the nutritional supply or to the therapeutic administration of a bone formation stimulating and/or bone resorption inhibiting composition.

STATE OF THE ART

Bone is not a static tissue. Bone experiences a constant remodeling resulting from the destruction, then synthesis de novo of the bone tissue within a complicated process implying two cellular main types, respectively the osteoblasts that provide for the new bone tissue and osteoclasts that destroy the bone substance.

A great number of cytokines and growth factors contribute to regulate the activity of such cells, most of them having been identified and cloned, as described in Mundy's general review (Mundy, G. R., 1996, Clin. Orthop., vol. 324:24-28; Mundy, G. R., 1993, J. Bone Miner Res, vol. 8: p 505-p 510).

Osteoblasts that are responsible for bone formation differentiate from precursor cells and express and secrete structural proteins such as type I collagen, as well as enzymes (alkaline phosphatase) and many regulating peptides and BMP (Bone Morphogenetic Proteins) (Stein G. and al., 1990, Curr. Opin Cell Biol. vol. 2: 1018-1027; Harris S and al., 1994, J. Bone Miner Res Vol. 9:855-863).

Osteoclasts are multinucleate cells that are responsible for bone loss within a process commonly referred to as bone resorption.

During the human or animal growth period, the so called bone acquisition predominates, that is to say the bone forming activity.

For humans or animals in adulthood, the balanced action of osteoblasts and osteoclasts makes it possible to maintain the bone mass in the long term and simultaneously ensures bone tissue remodeling by bone resorption, then bone synthesis de novo.

Nevertheless, as time goes on, the bone remodeling process becomes unbalanced, resulting in a bone loss that is referred to as osteopenia.

Age-related osteopenia is an universal phenomenon, that is not pathologic per se, but that builds up the osteoporosis basis since bone mass reduction represents the most important etiological factor in the genesis of this disease, which does not nevertheless exclude the influence of other parameters such as, for example, the skeletal architecture or the tendency to fall down.

This osteopenia, once exacerbated, indeed increases the breaking risk (bone mineral density under which the smallest impact may cause a fracture) which determines the osteoporosis occurrence. (Post-menopausal or senile) osteoporosis can hence be considered as being similar to an infantile pathology, the prophylaxis of which could be based on both (i) bone store optimization (acquired during the individual growth), and (ii) old age-induced bone loss slowing down.

There is a great heterogeneity amongst the peak bone mass values varying according to individuals because of changes in the bone growth process in the very beginning of life. That is the reason why the maximum bone mass reached before 30 years, also representing the peak bone mass, strongly varies from an individual to the other. As age progresses, individuals having a poor peak bone mass value are disadvantaged.

Therefore, an early personal caring has to be encouraged since the two crucial stages for bone stores are:
the growth period that permits the maximum bone mass to be acquired (peak bone mass);
aging, conditioning the bone mass loss rate.

So osteoporosis prevention should no more be limited to the elderly.

There are amongst pathological disorders associated with bone metabolism imbalance, especially osteoporosis, Paget's disease, bone loss or osteolysis observed in the vicinity of a prosthesis, metastatic bone diseases, cancer induced hypocalcemia, multiple myeloma, and periodontal diseases.

Some bone metabolism disorders or diseases may result from a long-lasting immobilization, for example after a hospitalization or after a weightlessness period.

There are other factors that may increase bone loss leading to osteoporosis, such as smoking, drug abuse, sedentarity, poor calcium intake, malnutrition or also vitamin D deficiency.

The most common disorder associated with an abnormal bone resorption is osteoporosis, the occurrence of which appears the most frequently in women, after the beginning of menopause. Osteoporosis is a systemic skeletal disease characterized by a bone mass reduction and a bone tissue microarchitecture degradation, associated with an increased bone fragility and with fracture sensitivity thereof.

According to the clinical classification selected as a reference by the World Health Organization, the bone general health of an individual is determined by the bone mineral density value, such as measured by bone mineral density test, as compared to a predetermined normal value.

An individual having a bone mineral density value of less than 1 SD (SD=standard deviation) as compared to the predetermined normal bone mineral density for a young adult is considered as being a "normal" individual (T-score>−1 SD, where "T-score" refers to the difference expressed in number of standard deviations SD between the individual bone mineral density and the bone mineral density mean value of a reference young adult population).

An individual having a bone mineral density value ranging from −1 to −2.5 SD as compared to the one of a young adult is classified as being an individual suffering from "osteopenia" (−1 SD>T-score>−2.5 SD).

An individual having a bone mineral density value under the one of a young adult by more than 2.5 SD is classified as being an individual suffering from osteoporosis (T-score-<−2.5 SD).

An individual having a bone mineral density value under the one of a young adult by more than 2.5 SD and for whom the occurrence of one or more fracture(s) has been detected is classified as being an individual suffering from confirmed osteoporosis. (T-score<−2.5 SD+fractures).

There are two different types of osteoporosis, osteoporosis of type I and osteoporosis of type II, respectively.

Type I osteoporosis is six times as frequent for women as compared to men. Type I osteoporosis mainly appears in a sub-group comprising menopausal women aged from 51 to 75 years, and is characterized by an excessive bone loss essentially in the bone trabecular substance. Vertebral element fractures and forearm lower end fractures represent traditional complications thereof. Type I osteoporosis is mainly associated with hormonal estrogenic deficiency of the menopause and to some extent of the andropause as well.

A large population of women and men over 70 years of age suffers from type II osteoporosis and is associated with collum femoris fractures, humerus and tibia upper end fractures, in other words bone sites that all comprise the cortical and the trabecular substance of bone. Parathormone circulation rates are often high. Type II osteoporosis is twice as frequent for women.

There are for humans or animals a plurality of conditions that are characterized by the need to increase bone formation. For example, in the case of bone fractures, bone growth must be stimulated in order to improve the complete bone repair. Such a need also applies in periodontal diseases, bone metastatic diseases, osteolytic diseases and conditions where connective tissue repair is expected, for example for cicatrizing or regenerating cartilage defects or traumatisms. Bone growth stimulating is also expected in the case of primary and secondary hyperparathyroidism, as well as in diabetes-related osteoporosis and in glucocorticoid-related osteoporosis, as well as in androgenic osteoporosis.

To date, strategies aiming at restoring an estrogenic impregnation (as well as an androgenic one, for men) using a hormone replacement therapy were strongly encouraged, especially to minimize the multiplicity of menopause functional signs and above all to reduce skeletal and vascular risks resulting from hormonal deficiency. Nevertheless, for many reasons (contra-indications, hormone prescription reservation, and so on), this prophylactic treatment type is prescribed to less than 30% menopausal women. This therapeutic abstention probably will further aggravate because of today's suspicion atmosphere as regards hormone therapy treatments, following the recent publication of two American studies revealing cardiovascular and cancerous risks (HERS, 1998, 2002; WHI, 2002).

Hulley S, Grady D, Bush T. Furberg C, Herrington D, Riggs B, Vittinghoff E, 1998 Randomized trial of estrogen plus progestin for secondary prevention of coronary heart disease in postmenopausal women. Heart and Estrogen/progestin Replacement Study (HERS) Research Group, JAMA 280(7):605-13.

Hulley S. Furberg C, Barrett-Connor E, Cauley J, Grady D, Haskell W. Knopp R, Lowery M, Satterfield S, Schrott H, Vittinghoff E, Hunninghake D, 2002 Non-cardiovascular disease outcomes during 6-8 years of hormone therapy: Heart and Estrogen/progestin Replacement Study follow-up (HERS II). Jama 288(1):58-66.

Rossouw J E, Anderson G L, Prentice R L, LaCroix A Z, Kooperberg C, Stefanick M L, Jackson R D, Beresford S A, Howard B V, Johnson K C, Kotchen J M, Ockene J, 2002 Women's health initiative Risks and benefits of estrogen plus progestin in healthy post menopausal women. JAMA 288:321-333.

Selective estrogenic receptor modulators (also abbreviated SERMs), such as raloxifene, are also recommended. However, they remain without any effect on hot flash incidence.

Synthetic steroids are also known, such as tibolone, having an estrogenous and progestational activity, with a poor androgenic property, but that may nevertheless cause leucorrhoea, vaginitis, mastodynia and result in a weight gain.

In fact, there is nowadays a plurality of compounds that are active in stimulating bone formation or bone resorption inhibition, comprising the polyphosphonate class, such as etidronate or alendronate (European patent n°EP 210 728, American patent application published-under serial number 2001/0046977), thioamide oxazolidinones (American patent application published under serial number 2002/0010341), or isoflavone compounds (American patent application published under serial number 2002/0035074). Using a Lycopersicon genus plant extract has also been proposed (American patent application published under serial number 2002/0009510).

Although many various active compounds now exist to stimulate bone formation and/or to prevent bone resorption, there is still a constant need for new active compounds, especially because of mixed success of nowadays treatments.

Moreover, since some bone metabolism imbalance-induced conditions have a chronic character, there is a need for new active compounds that could be used for a long period of time for humans or animals.

This explains why health specialists, as well as official entities in charge with regulatory affairs (European Community report on osteoporosis, 1998) recommend the integration of validated complementary therapies, or even alternative therapies. A nutritional approach (for example as a composition) fully satisfies these criteria.

SUMMARY OF THE INVENTION

Surprisingly, the applicant discovered that oleuropein, a compound especially comprised in plants of the oleaceae family, can act on bone metabolism by slowing down bone demineralization.

The present invention thus provides a nutritional composition and a pharmaceutical composition to be used for humans or animals comprising as active compound oleuropein or one derivative thereof.

The present invention further relates to the use of the oleuropein compound or one derivative thereof for making a composition to be used for stimulating bone mineralization, in particular bone formation and/or for inhibiting bone resorption for humans or animals.

According to a first aspect, the use hereabove is characterized in that said composition is a nutritional composition suitable for oral administration.

According to a second aspect, the use hereabove is characterized in that said composition is a pharmaceutical composition suitable for oral, parenteral, intramuscular or intravenous administration.

DETAILED DESCRIPTION OF THE INVENTION

Figure 1:
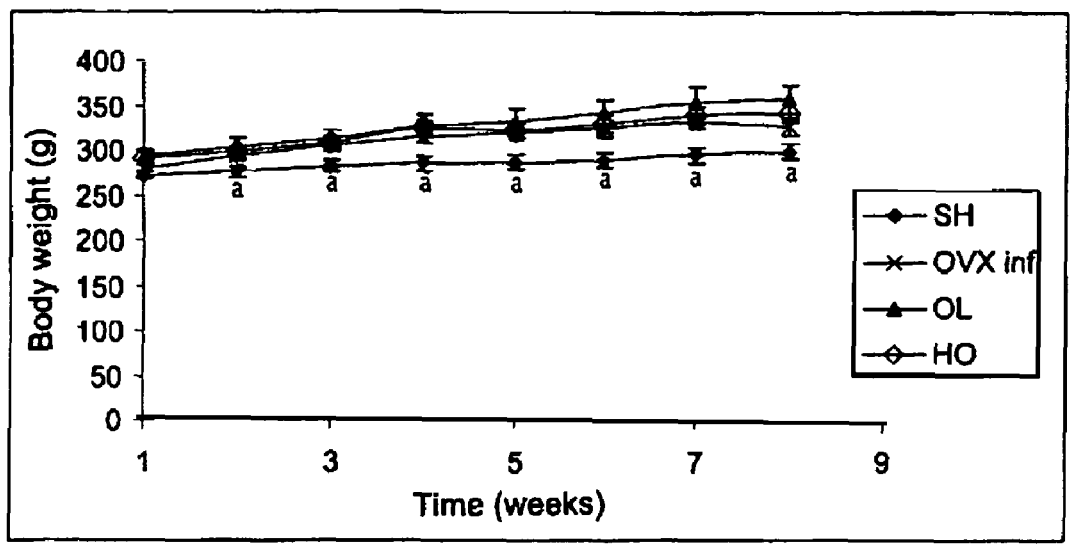
FIG. 1 illustrates the weight evolution (i) of control female rats (SH), (ii) of ovariectomized female rats, suffering from inflammation (OVX inf) and having a control diet, (iii) of "OVX inf" female rats having an oleuropein extract comprising diet (OL) and (iv) of "OVX inf" female rats having an olive oil comprising diet (HO). The rat mean body weight is represented in ordinates, and the treatment duration in abscissas, depending on the ovariectomy time.

The present invention provides a nutritional composition and a pharmaceutical composition to be used for humans or animals in order to stimulate bone mineralization, in particular to stimulate bone formation and/or to prevent bone resorption, for humans or animals and comprising as active compound the oleuropein compound or one derivative thereof.

Oleuropein is a bitter-taste glycoside which is especially found in the fruit, the roots, the trunk and more particularly in the leaves of plants belonging to the oleaceae family, and especially the *Olea europaea* family.

Oleuropein is well known for its anti-oxidizing and anti-inflammatory action, as well as for its antifungal, antibacterial and antiviral activities.

Oleuropein anti-inflammatory activity was evidenced through its capacity to inhibit the so called "oxidative burst" of neutrophilic polynuclear cells, which makes free radicals to be produced in excess during inflammatory reactions within the system.

Oleuropein, as well as some derivatives thereof, anti-virus activity, has been especially described in the PCT application n° WO 96/14064 and in the U.S. Pat. No. 6,455,580 and U.S. Pat. No. 6,117,844. Using oleuropein for treating influenza virus-mediated disorders has been described in the U.S. Pat. No. 6,455,070.

Using oleuropein for preparing pharmaceutical compositions in order to treat psoriasis has also been described, especially in the U.S. Pat. No. 6,440,465.

Surprisingly, it has been demonstrated according to the present invention that oleuropein stimulates bone formation and prevents bone resorption.

As described in the examples, oleuropein induces a density increase in metaphyseal bone tissue (bone trabecular substance) and in diaphyseal bone tissue (bone cortical substance), thereby providing a bone mineralization reinforcement, in particular in post-menopausal and senile osteoporosis experiment models.

More specifically, oleuropein inhibits bone resorption in ovariectomized female rats, which corresponds to the standard animal experiment model that mimics human osteoporosis.

It has further been revealed according to the present invention that oleuropein mediated bone tissue mineralization inducing effect was accompanied with an anti-inflammatory activity, as indicated by a plasma orosomucoid reduced concentration and by the lack of spleen weight gain, for ovariectomized animals, as illustrated in the examples.

This surprising combination of oleuropein biological properties makes it especially suitable for preventing or treating both type I and type II osteoporosis, frequently associated with inflammatory reactions.

Moreover, as illustrated in the examples, oleuropein does not present any detectable effect that mimics an estrogenic compound, also called "estrogen-like" effect, as indicated by the lack of weight gain in treated spleens, as well as oleuropein lack of effect on the uterine weight. These results confirm that oleuropein is interesting for preventing or treating any bone tissue disorder or for maintaining bone health, for humans or animals, since oleuropein bone mineralization inducing biological activity does not seem to be limited to situations wherein hormonal deficiency is observed or foreseen.

Such oleuropein bone mineralization induced activity makes it very useful as active compound for humans or animals in order to maintain or to restore bone metabolism balance, that is to say:

either to held at a constant level osteoblastic and osteoclastic cell activity as time goes on and age progresses and thus to prevent bone metabolism disorders;

or to counteract a bone metabolism imbalance, for example in the context of disorders such as osteoporosis, or to stimulate bone regeneration, for example in the case of bone fissure or fracture.

It is therefore an object of the present invention to provide the use of oleuropein compound or one derivative thereof for making a composition suitable for maintaining or restoring bone metabolism balance for humans or animals, by stimulating bone formation and/or by preventing bone resorption.

The present invention further relates to the use of the oleuropein compound or one derivative thereof for making a composition suitable for inhibiting bone tissue demineralization, for humans or animals.

As used herein, "oleuropein", refers to a compound of following formula (I):

(I)

[Chemical structure of oleuropein showing a dihydroxyphenyl group attached via a chain to a pyran ring system with COOMe group and O-Glu substituent]

As used herein, "oleuropein derivative", refers respectively to following compounds:
(a) elenolic acid of following formula (II):

(II)

[Chemical structure of elenolic acid]

(b) lactone of following formula (III):

(III)

[Chemical structure with R$_1$ and R$_2$ substituents on a phenol ring with ethyl chain]

wherein R$_2$ represents a hydroxyl group and R$_1$ represents hydrogen (tyrosol) or a hydroxyl group (hydroxytyrosol);
(c) lactone compound of following formula (IV):

(IV)

[Chemical structure of lactone compound IV]

(d) compounds of following formula (V):

(V)

[Chemical structure of compound V with R$_1$ and OR substituents]

wherein R represents a glycosyl group or a hydrogen atom; R$_1$ represents a 2-(3,4-dihydroxyphenyl)ethyl group, a 2-(4-hydroxyphenylethyl) group, a hydrogen atom or a methyl group;
(e) oleanic acid;
(f) products formed by hydrolysis of each compound of formula (I) to
(V) hereabove in the gastrointestinal tract.

Elenolic acid and hydroxytyrosol are oleuropein derivatives resulting from oleuropein metabolization within the system.

Compounds of formula (V) wherein R$_1$ represents the 2-(3,4-dihydroxyphenyl)ethyl group or the 2-(4-hydroxyphenylethyl) group are naturally found in plants belonging to the Olea europea family, for example in Olea europea varieties called Manzanillo and Mission.

Oleuropein derivative of formula (V) wherein R$_1$ represents the 2-(3,4-dihydroxyphenyl)ethyl group may be easily isolated from olive leaves (Olea europaea) by extraction in an aqueous solution or in a water/alcohol solution at a temperature ranging from 20° C. to 25° C., and more preferably at a temperature ranging from 40° C. to 100° C.

Oleuropein may be purified, for example using chromatography separating methods.

As an illustrative example, oleuropein may be prepared from Olea europaea leaves according to the teaching of the U.S. Pat. No. 5,714,150, using a method comprising following steps consisting in:
a) immersing *Olea europaea* leaves with an extraction solution essentially made of an alcoholic solution comprising at least 25% alcohol by weight, for example ethanol, for a period of time of at least 4 hours;
b) recovering the resultant extraction solution from end of step a);
c) immersing de novo *Olea europaea* leaves from step a) with a new extraction solution, which composition is similar to that defined hereabove, for a period of time of at least 4 hours;
d) recovering the extraction solution from end of step c);
e) collecting the resultant extraction solutions respectively from step b) and step c);
vacuum distillating the resultant solution from step e), for example at 70° C., so as to yield a concentrate comprising from 30% to 40% by weight of solids; and
g) drying the resultant concentrate from end of step f, for example by spraying at 70° C., so as to yield an extract as particles comprising from 30% to 40% by weight of the oleuropein compound.

Oleuropein may also be prepared by extraction from Olea europeae leaves according to the teaching of the American patent application published under serial number US 2003-0017217, Jan. 23rd 2003.

Oleuropein or anyone of its derivatives may also be prepared according to the teaching of the PCT application n° WO 96/14064 published May 17th 1996.

As used herein, "bone formation stimulation", refers, according to the present invention, to the ability of oleuropein or derivatives thereof to stimulate osteoblast activity and to thus boost bone protein matrix synthesis and mineral deposition, especially calcium deposition, onto this protein matrix, in other words to stimulate bone mineralization, also called bone accretion.

To make sure that oleuropein supply to a human or to an animal, in particular a mammalia, stimulates bone formation, the man skilled in the art will especially use ordinary densitometry measures and check that supplying oleuropein or one derivative thereof at a given dose indeed results in a bone density increase.

As used herein "bone resorption inhibition", refers according to the present invention to a blockage of the bone tissue destruction activity by osteoclast cells. To check that supplying oleuropein or one derivative thereof to humans or animals, prevents bone resorption, the man skilled in the art can measure the deoxypyridinoline urinary route excretion, deoxypyridinoline excretion reduction being an indication of a bone resorption inhibition (in: "Les marqueurs biologiques de remodelage osseux: variations pré-analytiques and recommandations pour leur utilisation", P. GARNERO, F. BIANCHI, P. C. CARLIER, V. GENTY, N. JACOB, S. KAMEL, C. KINDERMANS, E. PLOUVIER, M. PRESSAC & J. C. SOUBERBIELLE. Annales de Biologie Clinique, 58 (6), 683-704 (2000)).

Supplying oleuropein or one derivative thereof to an animal simultaneously induces a bone formation stimulation and a bone resorption inhibition, an overall bone mineralization increase, and hence that of bone density, resulting from the induction of both mechanisms.

To determine whether a patient suffers from osteopenia (reduced bone mass), and therefore needs to be supplied with oleuropein or one derivative thereof, the man skilled in the art could especially refer to the 1994 World Health Organization report called "Assessment of fracture risk and its application to screening for post-menopausal osteoporosis "WHO Technical Series-843".

A nutritional composition or a therapeutic composition comprising oleuropein or one derivative thereof as active compound is specifically to be used to prevent bone loss resulting from bone tissue remodeling imbalance, for humans or animals, in particular for a non human mammalia, especially a domestic mammalia such as the dog or the cat, or even the horse.

A composition such as defined hereabove is also to be used to boost the bone growth in young individuals so as to optimize the bone store acquisition. A composition according to the present invention is particularly useful during the growth period for humans as well as for other mammalias.

The oleuropein or one derivative thereof comprising composition is also to be used for individuals exhibiting bone deficiency symptoms (osteopenia), or that might suffer from bone deficiency, that is to say from an unbalanced bone formation/bone resorption ratio, which could induce a bone mass reduction, should it continue. A composition according to the present invention is further to be used for individuals exhibiting a clinical expression of the pathology, that is a fracture, or a dental disease.

In particular, a nutritional or a pharmaceutical composition to be used for humans or animals according to the present invention is useful for treating conditions such as type I or type II osteoporosis, secondary osteoporosis, Paget's disease, bone loss or osteolysis observed at the vicinity of a prosthesis, metastatic bone diseases, cancer induced hypocalcemia, multiple myeloma, periodontal diseases or osteoarthritis.

The fact that oleuropein induces an increase not only of the bone trabecular substance density, but also of the bone cortical substance density reveals the high biological activity level of such molecule.

Indeed, the bone trabecular substance, which forms the bone head and which is highly vascularized, is the most preferred site for exchanging calcium between the bone and the blood stream, whereas the bone cortical substance, which forms the straight body of the bone, is not very vascularized and thus represents a biological target that cannot be easily accessed with compounds stimulating bone formation and/or inhibiting bone resorption. Yet accessibility to the bone cortical substance with active compounds is important, since this bone tissue highly contributes to maintaining skeletal rigidity (biomechanical properties).

The composition according to the present invention may come as a nutritional composition or as a pharmaceutical composition as well, as will be described hereafter.

Nutritional Compositions Comprising Oleuropein or One Derivative Thereof

As it has already been mentioned hereabove, many disorders associated with a bone metabolism imbalance, such as osteoporosis, evolve progressively over a long period of time and need chronic treatments. They hence can be prevented or treated thanks to the regular supply with oleuropein or one derivative thereof, preferably in the form of a nutritional composition.

Similarly, a regular oleuropein nutritional supply to young growing individuals, whether humans or animals, shall ensure an optimization of the peak bone mass and therefore of the bone mineral density at adult age.

Similarly, a regular oleuropein nutritional supply is useful for preventing bone loss that occurs with aging.

It is an object of the present invention to provide a nutritional composition in order to stimulate bone formation and/or inhibit bone resorption, characterized in that it comprises, as active nutritional compound, the oleuropein compound or one derivative thereof.

As used herein "nutritional composition", refers according to the present invention, to a composition comprising oleuropein or one derivative thereof and representing a food composition or a food supplement that does not possess the characteristics of a drug.

The different uses of the oleuropein compound or one derivative thereof for making a nutritional composition will be defined hereafter in relation with technical characteristics of said nutritional composition.

A nutritional composition according to the present invention is preferably suitable for oral administration.

According to a first aspect, a nutritional composition according to the present invention is a food product used for keeping in good health the human or the animal supplied with it. Such a nutritional composition is also commonly referred as "functional food product", which is to be consumed, either as being an integral part of a diet, or as a food supplement, but which oleuropein or its derivative(s) content implies a physiological role beyond the simple answer to nutritive needs.

According to a first aspect, said nutritional composition is to be used for stimulating bone formation for young individuals in growth period.

According to a second aspect, said nutritional composition is to be used for preventing bone loss which occurs with aging (osteopenia).

According to a third aspect, said nutritional composition is to be used for preventing or for treating disorders associated with an unbalanced bone formation-bone resorption ratio.

According to a fourth aspect, said nutritional composition is to be used for treating a bone deficiency resulting from a fracture.

According to a further aspect, said nutritional composition is to be used for preventing conditions from the group consisting of type I or type II osteoporosis, secondary osteopenia, Paget's disease, bone loss or osteolysis observed in the vicinity of a prosthesis, metastatic bone diseases, cancer induced hypercalcemia, multiple myeloma, periodontal diseases or osteoarthritis.

A nutritional composition according to the present invention, characterized in that it comprises as active compound the oleuropein compound or one derivative thereof and that it comes in a great plurality of food composition and beverage forms, comprising juices (fruits or vegetables), oils, butters, margarines, vegetal fats, cans (for example tuna fish in oil), soups, milk-based preparations (yogurts, cottage cheese), ice creams, cheeses (for example oil-kept cheeses), baked products (such as bread, cookies and cakes), puddings, confectionary products, cereal bars, breakfast cereals, condiments, seasoning products (especially spices and dressings).

When oleuropein or one derivative thereof is extracted from the leaf, a nutritional composition according to the present invention is advantageously used as an aqueous solution.

When oleuropein or a derivative thereof is extracted from olive, a nutritional composition according to the present invention is advantageously used as an oily solution.

A nutritional composition according to the present invention, characterized in that it comprises as active compound the oleuropein compound or one derivative thereof, may also come as a variety of products for animal feeding, in either wet form or half-wet form or dry form, especially as biscuits.

As already mentioned hereabove, oleuropein is a major compound found in different parts, comprising leaves, of plants of the Oleaceae family, and more particularly in the leaves of plants belonging to Olea europaea genus (olive tree).

So, according to a preferred first aspect, the oleuropein compound or one derivative thereof comes as an extraction product from a plant belonging to the Oleaceae family. Preferably, the extraction product is a product extracted from the stems, the leaves, the fruits or the stones of a plant belonging to the Oleaceae family.

Preferably, the plant belonging to the Oleaceae family is selected from the group consisting of Olea europaea (olive tree), a plant of genus *Ligustrum*, a plant of genus *Syringa*, a plant of genus *Fraximus*, a plant of genus *Jasminum* and a plant of genus *Osmanthus*.

According to a preferred second aspect, the extraction product is olive oil or an oleuropein rich extract from olive oil.

According to a preferred third aspect, the extraction product is an extract from Olea europaea leaves, which comes in a liquid form or as a powder.

According to a fourth aspect, a nutritional composition according to the present invention may be a olive oil, or an olive oil or olive leaf extract-enriched food composition.

According to a fifth aspect, a nutritional composition according to the present invention comes as any product, in particular any beverage, for example a flavored beverage.

So, a nutritional composition according to the present invention, which is in liquid or in solid form, especially as a powder, may be an extraction product from olive oil or olive leaves, or may also comprise an extraction product from olive oil or olive leaves.

Especially, a nutritional composition according to the present invention comes as a beverage.

Generally, a nutritional composition according to the present invention comes as any form described in the present description, and in particular fat-base food products (butter, oil, margarine), bread, cookies, or oil kept food products, such as cheese, fish, meat, vegetables, or salads) or as seasoning products, such as condiments.

According to a further aspect, in a nutritional composition according to the present invention, oleuropein or one derivative thereof is produced by extraction or chemical synthesis.

Preferably, a nutritional composition according to the present invention comprises the oleuropein compound or one derivative thereof in an amount suitable for a daily oral administration ranging from 0.01 mg to 200 mg.

For human supply, a nutritional composition according to the present invention comprises an amount of active compound suitable for a daily supply of oleuropein or one derivative thereof provided by said composition, ranging from 0.01 mg to 200 mg, preferably from 0.1 mg to 200 mg and most preferably from 1 mg to 200 mg.

For animal supply, specifically a non human mammalia, a nutritional composition according to the present invention is suitable for a daily administration of active compound provided by said composition, ranging from 1 mg to 200 mg, preferably from 10 mg to 200 mg oleuropein or one derivative thereof.

According to a further aspect, the nutritional composition hereabove may comprise further nutritional compounds, in combination with oleuropein or one derivative thereof.

So, the nutritional composition according to the present invention may further comprise a calcium source, for example as an organic or inorganic physiologically acceptable compound, such as calcium inorganic salts (calcium chloride, calcium phosphate, calcium sulfate, calcium oxide, calcium hydroxide or calcium carbonate) or calcium comprising organic components such as powdered skim milk, calcium caseinate or calcium organic salts (calcium citrate, maleate or mixtures thereof).

The calcium amount comprised in a nutritional composition according to the present invention is suitable for a daily administration provided by said composition, ranging from 100 mg to 1000 mg, preferably from 200 mg to 700 mg and most preferably from 300 mg to 600 mg calcium.

A nutritional composition according to the present invention may further comprise vitamins, such as vitamin A, vitamin D, vitamin E, vitamin K, vitamin C, folic acid, thiamine, riboflavin, vitamin $B_6$, vitamin $B_{12}$, niacin, biotin or panthothenic acid.

A nutritional composition according to the present invention may further comprise minerals and trace elements such as sodium, potassium, phosphorus, magnesium, copper, zinc, iron, selenium, chromium and molybdenum.

It may further comprise soluble fibers such as agar-agar, alginate, locust bean, carragheenan, acacia gum, guar gum, karaya gum, pectin or xanthan gum, such soluble fibers being in hydrolyzed or non hydrolyzed form.

It may also comprise energetic source compounds, especially one or more carbon hydrate source(s) selected from the group consisting of maltodextrins, starch, lactose, glucose, sucrose, fructose, xylitol and sorbitol and optionally fatty acids such as omega-3.

Moreover, a nutritional composition according to the present invention may further comprise spices or aromatic herbs.

It may further comprise polyphenol type compounds, separated from oleuropein or derivative thereof.

As already mentioned hereabove, a composition to be used to stimulate bone formation or to inhibit bone resorption according to the present invention may also come as a pharmaceutical composition, as will be described below.

Human or Animal Pharmaceutical Composition According to the Present Invention

It as also an object of the present invention to provide a human or animal pharmaceutical composition for stimulating bone formation and/or for inhibiting bone resorption, characterized in that it comprises as active compound the oleuropein compound or one derivative thereof.

In particular, the present invention relates to the use of oleuropein or one derivative thereof for making a pharmaceutical composition to be used for humans or animals to prevent or to treat a disorder associated with a bone metabolism imbalance, that is to say a pharmaceutical composition suitable to stimulate bone formation and/or to inhibit bone resorption.

Using oleuropein for making a pharmaceutical composition will be hereafter described in association with technical characteristics of said pharmaceutical composition.

A pharmaceutical composition according to the present invention comprises as active compound oleuropein or one derivative thereof, in an amount suitable for stimulating bone formation or inhibiting bone resorption in individuals in need of such a treatment.

According to a first aspect, a pharmaceutical composition according to the present invention is useful for stimulating bone formation for young individuals, both humans and animals, being in growth period, so as to increase the bone density stored at the beginning of the adulthood.

According to a second aspect, a human or animal pharmaceutical composition according to the present invention is useful for preventing bone loss which occurs as aging progresses.

According to a third aspect, a human or animal pharmaceutical composition according to the present invention is useful for preventing or for treating disorders or conditions associated with an unbalanced bone formation-bone resorption ratio.

According to a fourth aspect, a human or animal pharmaceutical composition according to the present invention is useful pour treating a bone deficiency resulting from a fracture.

According to a fifth aspect, a pharmaceutical composition to be used for humans or animals according to the present invention is useful for treating conditions associated with an unbalanced bone remodeling, such as, type I or type II osteoporosis, secondary osteoporosis, Paget's disease, bone loss or osteolysis observed at the vicinity of a prosthesis, metastatic bone diseases, cancer induced hypercalcemia, multiple myeloma, periodontal diseases or osteoarthritis.

II can be a human or animal pharmaceutical composition, in particular for dogs, cats or horses.

The pharmaceutical composition according to the present invention comes in a form suitable for oral, parenteral, intramuscular or intravenous administration.

In its form suitable for human administration, a pharmaceutical composition according to the present invention advantageously comprises oleuropein or one derivative thereof in an amount suitable for a daily administration of the active compound provided by said composition ranging from 0.01 mg to 200 mg.

In its form suitable for animal administration, a pharmaceutical composition according to the present invention comprises oleuropein or one derivative thereof in an amount suitable for a daily administration of the active compound provided by said composition, ranging from 1 mg to 200 mg.

A pharmaceutical composition according to the present invention comprises oleuropein or one derivative thereof in association with at least one excipient selected from the pharmaceutically acceptable excipients.

Methods for preparing the pharmaceutical compositions according to the present invention can be easily found by the man skilled in the art, for example in Remington's Pharmaceutical Sciences, Mid. Publishing Co, Easton, Pa., USA.

Physiologically acceptable adjuvants, vehicles and excipients are also described in "Handbook of Pharmaceutical Excipients", Second edition, American Pharmaceutical Association, 1994.

To formulate a pharmaceutical composition according to the present invention, the man skilled in the art will advantageously refer to the last edition of the European Pharmacopoeia or the American Pharmacopoeia (USP).

The present invention further relates to the use of an oily oleuropein extract as excipient for preparing a pharmaceutical composition (combination with other actives, for example).

The man skilled in the art will especially advantageously refer to the fourth edition "2002" of the European Pharmacopoeia, or to the USP 25-NF 20 edition of the American Pharmacopoeia.

A pharmaceutical composition such as defined hereabove is suitable for oral, parenteral, intramuscular or intravenous administration.

When the pharmaceutical composition according to the present invention comprises at least one pharmaceutically or physiologically acceptable excipient, it is in particular an appropriate excipient so that the composition can be administrated via the oral route or via the parenteral route.

The present invention further relates to a method for preventing or treating a disorder associated with a bone metabolism imbalance, in particular a disorder associated with a bone mass loss, said method comprising a step consisting in administering to patients a therapeutically effective amount of oleuropein or one derivative thereof, or of a pharmaceutical composition comprising oleuropein or one derivative thereof.

A pharmaceutical composition comprising oleuropein or one derivative thereof according to the present invention can be either in a solid or in a liquid form.

For oral administration, a solid pharmaceutical composition is preferred, which comes as tablets or capsules.

In its liquid form, the pharmaceutical composition will preferably be an aqueous suspension or an oily suspension or even a water-in-oil or a oil-in-water emulsion.

Solid pharmaceutical forms may comprise, as vehicles, adjuvants or excipients, at least a diluent, a flavoring agent, a solubilizing agent, a lubricant, a suspending agent, a binder, a disintegrant and a capsulating agent, the identity and the function of these various traditional excipients being exhaustively documented in the European Pharmacopoeia or in the American Pharmacopoeia (USP).

Such compounds are for example magnesium carbonate, magnesium stearate, talc, lactose, pectin, dextrin, starch, gelatin, cellulose materials, cocoa butter, and so on.

Compositions in liquid form may further comprise water, if appropriate in admixture with propylene glycol or polyethylene glycol, and optionally colorants, flavors, stabilizers and thickening agents as well.

For making a pharmaceutical composition according to the present invention, oleuropein or one derivative thereof may be prepared according to the teaching of various patents mentioned hereabove in the specification.

The present invention will be further illustrated, without being limited, by the following examples.

EXAMPLES

The results of the examples demonstrate oleuropein or olive oil osteoprotecting effects on a bone loss animal model representative of senile osteoporosis by inducing a chronic inflammation (aging) coupled with an ovariectomy (menopausal condition).

A. Material and methods

The experiment was conducted on 40 female rats Wistar aged 6 months, amongst which thirty were ovariectomized (OVX) and 10 pseudo-operated (SH). Animals were placed in metabolic cages enabling to separately collect the urines at a controlled temperature of 21±1° C., according to a 12 h-12 h nyctohemeral cycle. Following the surgical operation at Day0, animals were accustomed for seven days to a basic semisynthetic diet (INRA, Jouy-en-Josas, France), supplemented with 2.5% groundnut oil and 2.5% rapeseed oil and humidified to 1 ml water per gram powder. At the end of this adaptation period, the rats were separated in four homogeneous batches according to weight parameters and were fed for 72 days 22 g per day of following diets:
- Batch SH/10 pseudo-operated female rats fed control diet (basic diet supplemented with 2.5% groundnut oil and 2.5% rapeseed oil),
- Batch OVXinf: 10 ovariectomized female rats fed control diet,
- Batch OL: 10 ovariectomized female rats fed control diet supplemented with 0.015% oleuropein.
- Batch HO: 10 ovariectomized female rats fed basic diet supplemented with 5% extra-virgin olive oil.

Oil storage was kept away from light. Feed was prepared once a week and stored at +4° C.

At D55, that is 3 weeks before the end of the experiment, an inflammation was induced in each batch, except in control batch (SH). Four talc subcutaneous injections (3.2 g magnesium silicate (Sigma) suspended in 0.71 g/ml physiological saline) were administrated in 4 distinct sites of the animal back.

The day of sacrifice (D80), animals were anesthetized with a chloral intraperitoneal injection (Fluka/8% solution, 0.4 ml/100 g of live weight). Blood samples were collected at abdominal aorta for dosing orosomucoid (inflammation marker, in particular of the acute phase for humans and rats (Fournier and al. 2000), that is produced by lever and other extra-hepatic sites under the control of $II_1$, $TNF\alpha$ and $II_6$ cytokines).

Spleen and uterus were weighted.

Femurs were collected and removed from adjacent soft tissues, then kept in 80% ethanol for bone density determination.

B. Results

Example 1

Figure 2:
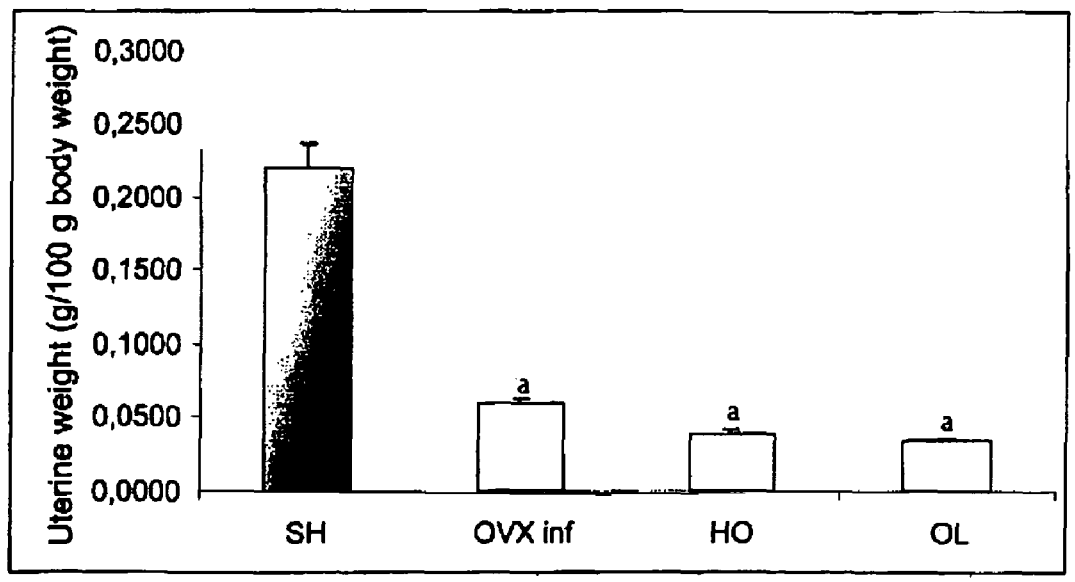
FIG. 2 illustrates the uterine weight (i) of the control female rats (SH), (ii) of the ovariectomized female rats, suffering from inflammation (OVX inf) and having a control diet, (iii) of "OVX inf" female rats having an olive oil comprising diet (HO), and (iv) of "OVX inf" female rats having an oleuropein extract comprising diet (OL). The rat mean uterine weight is represented in ordinates +/− standard error as compared to the mean value (SEM); and each group of female rats in abscissas. For batches OVX inf, HO and OL, *p<0.0001 as compared to the control group SH.

Body Weight and Uterine Weight (FIGS. 1 and 2)

The animal weight profile indicated a similar evolution, that is to say an increase occurring between the beginning and the end of the experimental period, whatever group being considered. Nevertheless, as early as the second week, the weight (g) of ovariectomized animals is higher than SH one (OVXinf: 294±6; SH/275±6. p=0.001). This phenomenon is not corrected by any of the two diets.

The uterine weight (g uterus/100 g body weight) is reduced for OVxinf (osteoporosis experiment model) (SH/ 0.221±0.017; OVX/0.060±0.003; p<0.001). It is not restored by any of the oleuropein (0.034±0.001) or olive oil (0.039±0.002) diets which thus are free from any uterotrophic effect.

Example 2

Figure 3:
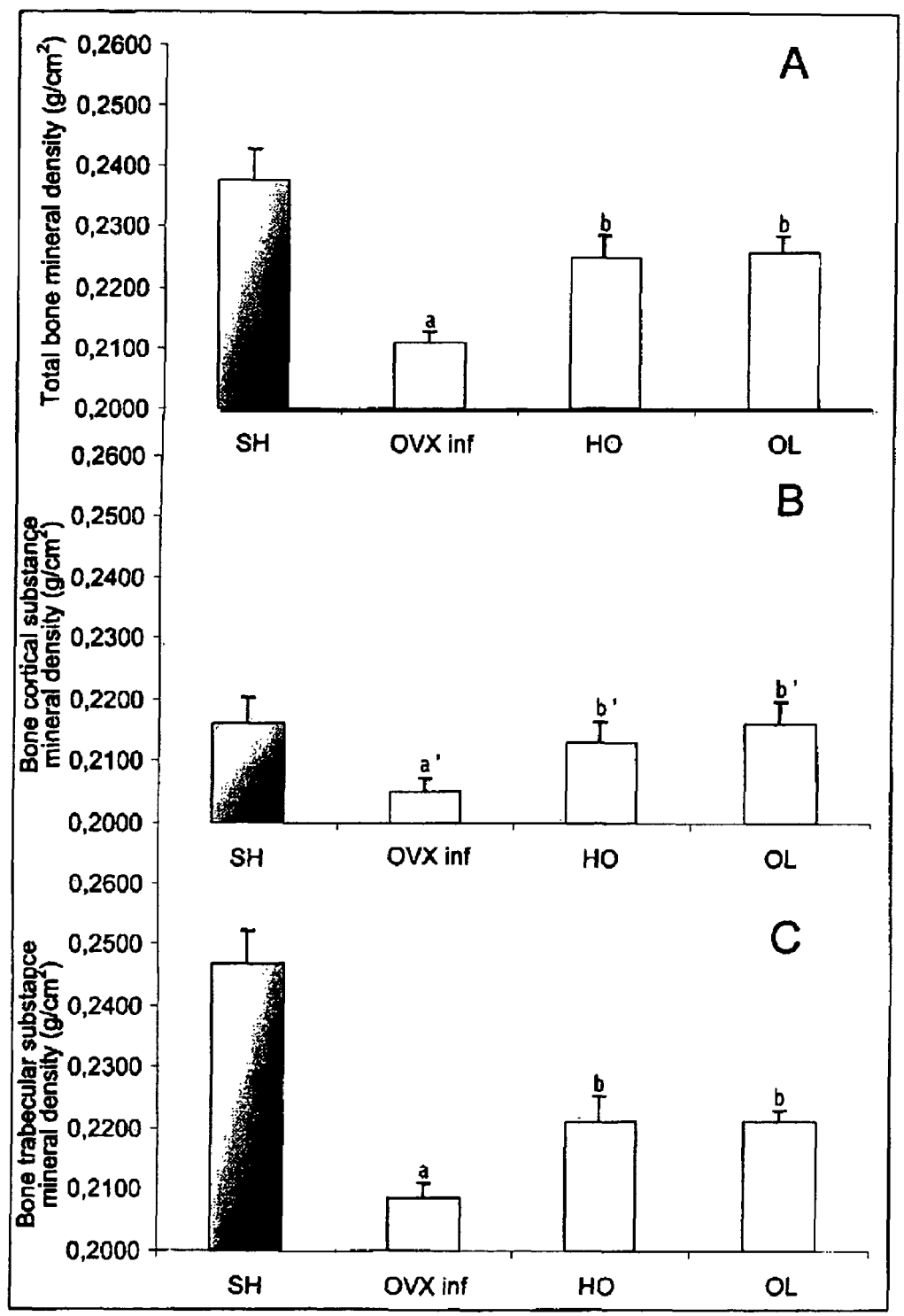
FIG. 3 illustrates the total bone mineral density (FIG. 3A), the bone cortical substance mineral density (FIG. 3B) and the bone trabecular substance mineral density (FIG. 3C), respectively (i) of the control female rats (SH), (ii) of the ovariectomized female rats, suffering from inflammation (OVX inf) and having a control diet, (iii) of "OVX inf" female rats having an olive oil comprising diet (HO), and (iv) of "OVX inf" female rats having an oleuropein extract comprising diet (OL). The bone mineral density, as expressed in $g/cm^2$ +/− standard error as compared to the mean value (SEM) is represented in ordinates; and each group of female rats is represented in abscissas. "a": $p<0.001$ as compared to the control group SH. "a'": $p<0.01$ as compared to the control group SH. "b": $p<0.005$ as compared to the group OVX inf. "b'": $p<0.05$ as compared to the group OVX inf.

Bone Mineral Density (FIG. 3)

Femur bone demineralization indicated an inflammation associated ovariectomy, demonstrated with a reduced total bone mineral density (g/cm$^2$) (SH: 0.2378±0.0050; OVXinf: 0.2109±0.0018 p<0.001). Such a process is (at least partly) prevented by supplying olive oil (0.2249±0.0038) or oleuropein (0.2258±0.0028).

A similar profile is demonstrated at trabecular substance level, as well as in the bone cortical substance (a tissue that is normally no very sensitive to environmental factors).

Example 3

Figure 4:
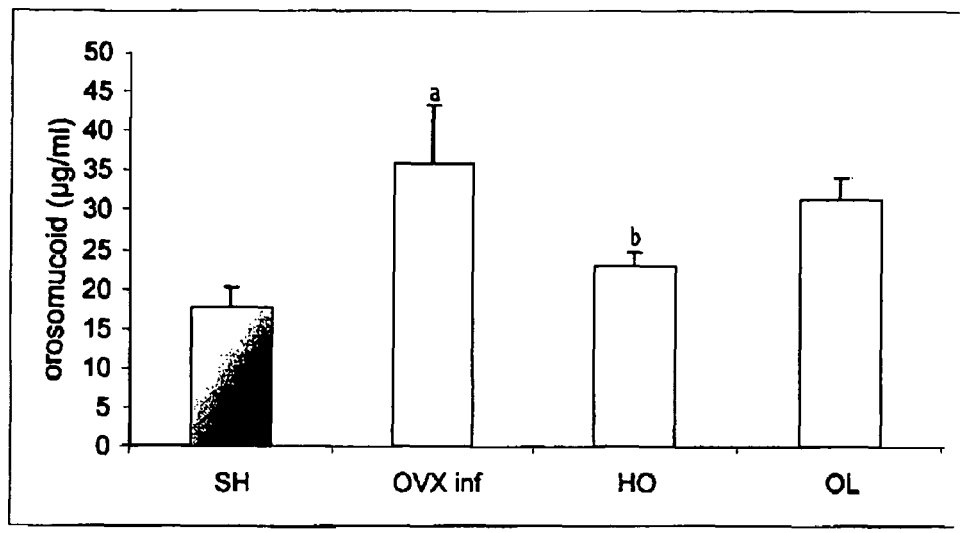
FIG. 4 illustrates the orosomucoid plasma concentration (i) of the control female rats (SH), (ii) of the ovariectomized female rats, suffering from inflammation (OVX inf) and having a control diet, (iii) of "OVX inf" female rats having an olive oil comprising diet (HO), and (iv) of "OVX inf" female rats having an oleuropein extract comprising diet (OL). The orosomucoid concentration, as expressed in $\mu g/ml$, +/− standard error as compared to the mean value (SEM) is represented in ordinates; and each group of female rats is represented in abscissas. "a": $p<0.05$ as compared to the control group SH; "b": $p<0.01$ as compared to the group OVX inf.
Figure 5:
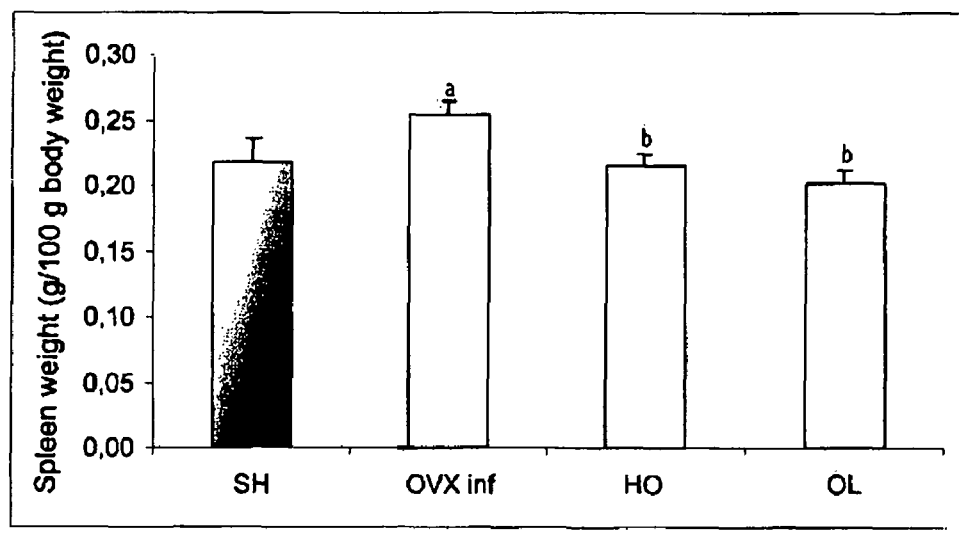
FIG. 5 illustrates the spleen weight (i) of the control female rats (SH), (ii) of the ovariectomized female rats, suffering from inflammation (OVX inf) and having a control diet, (iii) of "OVX inf" female rats having an olive oil comprising diet (HO), and (iv) of "OVX inf" female rats having an oleuropein extract comprising diet (OL). The spleen mean weight +/− standard error as compared to the mean value (SEM) standard error as compared to the mean value (SEM) is represented in ordinates; and each group of female rats is represented in abscissas. "a": $p<0.05$ as compared to the control group SH; "b": $p<0.01$ as compared to the group OVX inf.

Inflammation Markers (FIGS. 4 and 5)

Orosomucoid concentration (μg/ml) is higher for OVXinf: 35.9±7.5; SH: 17.8±2.4). This parameter is restored for female rats having been fed the olive oil diet (22.8±1.7 p<0.005). A similar (but not significant) tendency has been observed with the oleuropein diet.

The spleen weight (g spleen/100 g body weight) was increased for OVXINF (OVX inf: 0.254±0.009; SH: 0.219±0.018). This splenomegaly is prevented with supplying olive oil (0.215±0.009, p<0.01) or oleuropein (0.201±0.011 p<0.02).

The invention claimed is:

1. A method for stimulating bone formation and/or inhibiting bone resorption in humans or animals comprising the administration of a composition comprising oleuropein as active compound to a subject in need thereof suffering from a condition selected from the group consisting of type I or type II osteoporosis, secondary osteoporosis, osteolysis observed at the vicinity of a prosthesis, periodontal disease, osteoarthritis, and osteopenia.

2. The method according to claim 1, wherein the composition is a nutritional composition suitable for oral administration.

3. The method according to claim 2, wherein the subject in need thereof is suffering from a condition selected from the group consisting of type I or type II osteoporosis, and secondary osteoporosis.

4. The method according to claim 2, wherein the nutritional composition is selected from the group consisting of food compositions and beverages.

5. The method according to claim 2, wherein the nutritional composition is a product for animal feeding, in a wet, half-wet, or dry form.

6. The method according to claim 2, wherein the oleuropein or derivative thereof is an extraction product from a plant belonging to the Oleaceae family.

7. The method according to claim 6, wherein the extraction product is a product extracted from the stems, the leaves, the fruits or the stones of a plant belonging to the Oleaceae family.

8. The method according to claim 6, wherein the plant belonging to the Oleaceae family is selected from the group consisting of *olea europaea*, a plant of genus *Ligustrum*, a plant of genus *Syringa*, a plant of genus *Fraximus*, a plant of genus *Jasminum*, and a plant of genus *Osmanthus*.

9. The method according to claim 6, wherein the extraction product is an olive oil or an oleuropein rich extract of olive oil or leaves.

10. The method according to claim 2, wherein the nutritional composition is orally administered daily in an amount ranging from 0.01 to 200 mg of the oleuropein or derivative thereof.

11. The method according to claim 1, wherein the composition is a human or animal pharmaceutical composition.

12. The method according to claim 11, wherein the pharmaceutical composition is in a suitable form for oral, parenteral, intramuscular or intravenous administration.

13. The method according to claim 11, wherein the pharmaceutical composition is suitable for a daily oral administration in an amount ranging from 0.01 to 200 mg of the oleuropein or derivative thereof.

14. The method according to claim 4, wherein the nutritional composition is selected from the group consisting of fruit juices, vegetable juices, oils, butters, margarines, vegetal fats, canned foods, soups, milk-based-foods, ice creams, cheeses, baked products, puddings, confectionary products, cereal bars, breakfast cereals, condiments, and seasoning products.

15. The method according to claim 14, wherein the nutritional composition is selected from the group consisting of tuna fish in oil, yogurts, cottage cheese, oil-kept cheeses, bread, cookies and cakes, spices and dressings.

* * * * *